United States Patent
Luciow et al.

(10) Patent No.: US 8,148,309 B2
(45) Date of Patent: Apr. 3, 2012

(54) ACRYLIC POLYMER BASED PERSONAL CLEANSING COMPOSITION HAVING HIGH TRANSPARENCY, AND METHOD OF MAKING

(75) Inventors: Chris Luciow, Tempe, AZ (US); Evangeline Eng, Phoenix, AZ (US)

(73) Assignee: The Dial Corporation, Scottsdale, AZ (US)

( * ) Notice: Subject to any disclaimer, the term of this patent is extended or adjusted under 35 U.S.C. 154(b) by 565 days.

(21) Appl. No.: 12/298,711

(22) PCT Filed: Apr. 30, 2007

(86) PCT No.: PCT/US2007/067818
§ 371 (c)(1),
(2), (4) Date: Jul. 7, 2009

(87) PCT Pub. No.: WO2007/127987
PCT Pub. Date: Nov. 8, 2007

(65) Prior Publication Data
US 2009/0305929 A1    Dec. 10, 2009

Related U.S. Application Data

(60) Provisional application No. 60/745,930, filed on Apr. 28, 2006.

(51) Int. Cl.
C11D 1/94    (2006.01)
C11D 3/37    (2006.01)
C11D 3/43    (2006.01)

(52) U.S. Cl. ........ 510/147; 510/119; 510/123; 510/125; 510/127; 510/130; 510/155; 510/156

(58) Field of Classification Search .............. 510/147, 510/119, 123, 125, 127, 130, 155, 156
See application file for complete search history.

(56) References Cited

U.S. PATENT DOCUMENTS

| | | | | |
|---|---|---|---|---|
| 6,106,816 A | * | 8/2000 | Hitchen | 424/70.16 |
| 6,113,892 A | * | 9/2000 | Newell et al. | 424/70.19 |
| 6,593,856 B1 | * | 7/2003 | Madau | 340/12.27 |
| 2005/0049172 A1 | * | 3/2005 | Lukenbach et al. | 510/477 |
| 2010/0210497 A1 | * | 8/2010 | Walters et al. | 510/130 |

\* cited by examiner

*Primary Examiner* — Charles Boyer
(74) *Attorney, Agent, or Firm* — David K. Benson

(57) ABSTRACT

A composition and method for a cross-linked acrylic acid polymer based personal cleanser having high clarity is disclosed. Particular compositional ingredients are combined in a specified process such that the final composition comprises a clear, transparent personal cleansing product.

32 Claims, No Drawings

ACRYLIC POLYMER BASED PERSONAL CLEANSING COMPOSITION HAVING HIGH TRANSPARENCY, AND METHOD OF MAKING

CROSS-REFERENCE TO RELATED APPLICATION

This is the U.S. national phase application of International Application No. PCT/US2007/067818, filed 30 Apr. 2007, which claims the benefit of U.S. Provisional Application No. 60/745,930, filed 28 Apr. 2006.

FIELD OF INVENTION

The present invention relates to a personal cleansing composition and method of process. More particularly, the present invention relates to an acrylic polymer based personal cleanser that exhibits a high degree of transparency.

BACKGROUND OF THE INVENTION

Acrylic acid polymer based cleansing compositions are typically processed by first adding an acrylic acid polymer to water. This is followed by adding primary surfactants, a neutralizer, amphoteric and/or nonionic surfactants, conditioning ingredients (including cationic polymers), fragrance, dyes, and preservatives.

These general cleansing compositions based upon such acrylic acid polymers tend to exhibit a slightly hazy or not completely "optically" clear or transparent appearance. In addition, cationic ingredients and polymers, for example, polyquaternium-10, can counteract product clarity in acrylic acid polymer based cleansing formulations.

In addition to aesthetic value, it has been found that consumers' perceptions of beneficial personal cleansing compositions are directly related to the opacity of the product. If a product is intended have a "clear" on-shelf appearance, it has been found that the more transparent or clear a product is, the more people perceive the product to have beneficial qualities. Thus, there is a need in the market for a composition and method of process for an acrylic polymer based personal cleansing composition that contains a cationic polymer, wherein the composition exhibits high transparency properties.

SUMMARY OF THE INVENTION

This summary of the invention section is intended to introduce the reader to aspects of the invention. Particular aspects of the invention are pointed out in other sections herein below, and the invention is set forth in the appended claims which alone demarcate its scope. In accordance with an exemplary embodiment of the present invention, a personal cleansing composition is provided for use as a bodywash, cream, gel, lotion, shampoo, and the like. An exemplary cleansing composition includes a cross-linked acrylic acid polymer, an amphoteric and/or nonionic surfactant, an anionic surfactant, a cationic polymer, an ester, a high level of a polyol, and a polyethylene glycol. These components, when combined in the disclosed ratios with the disclosed unique process, deliver the high visual clarity formula.

DETAILED DESCRIPTION

The detailed description of various exemplary embodiments of the invention herein makes reference to exemplary compositions and methods of process for producing such compositions. While these exemplary embodiments are described in sufficient detail to enable those skilled in the art to practice the invention, it should be understood that other embodiments may be realized, and that logical and processing changes may be made without departing from the spirit and scope of the invention. Thus, the detailed description herein is presented for purposes of illustration only and not of limitation.

Turning now to the present invention, in accordance with various exemplary embodiments, the present invention comprises a personal cleansing composition comprising one or more of each of: a cross-linked acrylic acid polymer, an amphoteric and/or nonionic surfactant, an anionic surfactant, a cationic polymer, an ester including glyceryl esters, and a high level of a polyol. Moreover, it has been found that the addition of polyethylene glycol, in the range of from about 6 to about 12 moles of ethoxylation, provides an additional, unexpected, clarity benefit. These components, when combined in the disclosed ratios with the disclosed unique process, result in a highly transparent product. All percentages disclosed herein are based on total weight of the personal cleansing composition, unless otherwise indicated.

Cross-Linked Acrylic Acid Polymer

In an exemplary embodiment, the composition disclosed herein comprises one or more of a cross-linked acrylic acid polymer. Exemplary polymers include acrylates copolymer, acrylates/C10-30 alkyl acrylate cross polymer, and the like. In accordance with an exemplary embodiment, one or more of a cross-linked acrylic acid polymer is present in an amount of from about 0.4% to about 5.8%. More preferably, one or more of a cross-linked acrylic acid polymer is present in an amount of from about 0.8% to about 2.9%.

Amphoteric and/or Nonionic Surfactant

In an exemplary embodiment, the composition disclosed herein comprises one or more of an amphoteric and/or nonionic surfactant. Exemplary surfactants include cocamidopropyl betaine, cocamidopropyl hydroxysultaine, disodium laureth sulfosuccinate, decyl glucoside, sodium cocoamphoacetate, and the like. In accordance with an exemplary embodiment, one or more of an amphoteric and/or nonionic surfactant is present in an amount of from about 0.5% to about 16.0%. More preferably, one or more of an amphoteric and/or nonionic surfactant is present in an amount of from about 1.0% to about 8.0%.

Anionic Surfactant

In an exemplary embodiment, the composition disclosed herein comprises one or more of an anionic surfactant. Exemplary anionic surfactants include sodium or ammonium lauryl sulfate, sodium or ammonium laureth sulfate, and the like. In accordance with an exemplary embodiment, one or more of an anionic surfactant is present in an amount of from about 0.5% to about 16.0%. More preferably, one or more of an anionic surfactant is present in an amount of from about 1.0% to about 8.0%.

Cationic Polymer

In an exemplary embodiment, the composition disclosed herein comprises one or more of a cationic polymer. Exemplary polymers include quaternary ammonium hydroxyethyl cellulose and guar derivatives, and the like. In accordance with an exemplary embodiment, one or more of a cationic polymer is present in an amount of from about 0.05% to about 1.0%. More preferably, one or more of a cationic polymer is present in an amount of from about 0.10% to about 0.50%.

Ester Including Glyceryl Esters

In an exemplary embodiment, the composition disclosed herein comprises one or more of an ester including glyceryl esters. Exemplary esters include glyceryl oleate and PEG-7 glyceryl cocoate, and the like. In accordance with an exemplary embodiment, one or more of an ester is present in an amount of from about 0.05% to about 3.60%. More preferably, one or more of an ester is present in an amount of from about 0.10% to about 1.80%.

Polyol

In an exemplary embodiment, the composition disclosed herein comprises one or more of a polyol. Exemplary polyols include glycerin, sorbitol, lactose, and the like. In accordance with an exemplary embodiment, one or more of a polyol is present in an amount of from about 0.5% to about 10.0%. More preferably, one or more of a polyol is present in an amount of from about 1.0% to about 5.0%.

Polyethylene Glycol

In an exemplary embodiment, the composition disclosed herein comprises one or more of a polyethylene glycol. In various exemplary embodiments, a polyethylene glycol used within the scope of the present invention is in the range of from about 6 to about 12 moles of ethylene oxide. In accordance with an exemplary embodiment, one or more of a polyethylene glycol is present in an amount of from about 1.0% to about 20.0%. More preferably, one or more of a polyethylene glycol is present in an amount of from about 2.0% to about 10.0%.

Weight Ratios

In accordance with various exemplary embodiments of the present invention, the personal cleansing composition disclosed herein comprises: a weight ratio of anionic surfactant to cross-linked acrylic acid polymer in the range from about 2.5:1 to about 0.08:1; and a weight ratio of polyethylene glycol to cross-linked acrylic acid polymer in the range from about 12.5:1 to about 0.70:1. Though not wishing to be bound by any theory, it is believed weight ratios within the above ranges contribute to the "optically" clear or transparent appearance of personal cleansing compositions based upon acrylic acid polymers as disclosed herein.

Fragrance

In an exemplary embodiment, the composition disclosed herein comprises one or more of a fragrance. Exemplary fragrances include Parfum and the like. In accordance with an exemplary embodiment, one or more of a fragrance is present in an amount of from about 0.25% to about 4.0%. More preferably, one or more of a fragrance is present in an amount of from about 0.50% to about 2.0%.

Additional Additives

In other exemplary embodiments of the present invention, the composition may further comprise one or more other conventional additives such as a coloring agent (e.g., a dye), a water softening agent (e.g., a builder or chelating agent), a UV absorber, a pH modifier, a preservative, an odor absorber, a viscosity modifier, a neutralizer, a cationic conditioning polymer, an antibacterial agent, a vitamin, a botanical extract, a skin conditioner (e.g. an ester), a moisturizer (e.g., a humectant) and/or mixtures thereof.

One or more of such additives may be present in any amount suitable to achieve a particular objective. Any effective amount of additional additives, alone or combined may be utilized in accordance with the present invention insofar as such additives do not detrimentally affect the desired properties of the detergent composition.

Exemplary embodiments of the highly transparent personal cleansing composition of the present invention, with each of the components set forth in active weight percent of the total personal cleansing composition, are as follows:

| Component | Formula A wt. % | Formula B wt. % |
| --- | --- | --- |
| Water (D.I) | 67.05 | 65.79 |
| Polyquaternium-10 | 0.20 | 0.30 |
| Glycerin (99%) | 3.50 | 3.50 |
| Coco-Glucoside (and) Glyceryl Oleate | 0.60 | 0.40 |
| PEG-7 Glyceryl Cocoate | 0.50 | 0.75 |
| Disodium Laureth Sulfosuccinate | 2.50 | * |
| Sodium Laureth Sulfate | 5.40 | 5.40 |
| Decyl Glucoside | 0.25 | 4.00 |
| DMDM Hydantoin | 0.10 | 0.10 |
| Tetrasodium EDTA | 0.02 | 0.02 |
| Water (D.I) | 1.00 | 1.00 |
| Dyes | 0.000120 | 0.000120 |
| Fragrance | 1.25 | 1.25 |
| PEG-8 | 2.00 | 3.00 |
| Mica (and) Titanium Dioxide | 0.02 | * |
| Cocamidopropyl Betaine | 2.60 | 1.50 |
| Polyethylene | 0.25 | 0.25 |
| Polyethylene | 0.25 | 0.25 |
| Silica | 0.10 | * |
| Water (D.I) | 10.00 | 10.00 |
| Acrylates Copolymer | 2.10 | 2.10 |
| Sodium Hydroxide, 50% | 0.29 | 0.29 |
| Citric Acid, Anhydrous | 0.02 | * |

Method of Process

Turning now to an exemplary method of process, in formulating the transparent personal cleansing composition of the present invention, the composition is first formulated using a 316 L stainless steel mixing tank, or comparable vessel, with side sweep agitation, into which the batch quantity of water is added to such cool batch tank. Next, the cationic polymer is added to the water and mixed.

Next, a pH modifier is added, such as Tetrasodium EDTA for polyquaternium-10 or citric acid for cationic guar derivatives. This accelerates the hydration of the cationic polymer. Heating the batch to about 100° F. through the final processing step is subsequently carried out.

Next, a polyol, such as glycerin, esters, amphoteric surfactants (other than the secondary surfactant), and an anionic surfactant (primary surfactant) are added. As the product is continually mixed, additional compositional elements are added; polyethylene glycol (note: solid ingredients, such as beads can be premixed into this ingredient, for easier incorporation with minimal aeration); preservative and dyes; the cross-linked acrylic acid polymer; fragrance; viscosity modifiers, such as sodium chloride; and sodium hydroxide, or other strong base material, to neutralize cross-linked acrylic acid polymer.

It is believed that since the base viscosity is lower prior to adding the cross-linked acrylic acid polymer, adding the polyethylene prior to the cross-linked acrylic acid polymer will ensure even distribution of solids, with minimal aeration to the batch. Adding the cross-linked acrylic acid polymer subsequent to polyethylene is believed to ensure all solids (mica, polyethylene and silica) are entrapped and suspended uniformly. Again not wishing to be bound by any theory, it is believed the abovementioned method of process aspect contributes to the "optically" clear or transparent appearance of personal cleansing compositions based upon cross-linked acrylic acid polymers as disclosed herein.

Finally, the mixing agitation is paused and the secondary amphoteric surfactant is added to provide for the final thickening; the mixing agitation is resumed and mixed for 20 minutes. The cleansing composition, when combined in the disclosed ratios with the disclosed unique process, delivers the high visual clarity formula.

It will be understood that the foregoing description is of preferred exemplary embodiments of the present invention, and that the present invention is not limited to the specific examples and compositions set forth herein. Such examples and compositions are for illustrative purposes only. Various modifications may be made in light thereof as will be suggested to persons skilled in the art without departing from the scope of the invention.

We claim:

1. A highly transparent personal cleansing composition comprising:
    a) a cross-linked acrylic acid polymer;
    b) at least one of an amphoteric or nonionic surfactant;
    c) an anionic surfactant;
    d) a cationic quaternary ammonium compound polymer;
    e) an ester;
    f) a polyol which is different from component (g); and
    g) a polyethylene glycol in an amount of from about 2.0 to about 10.0 weight percent of the composition,
    wherein the weight ratio of anionic surfactant to cross-linked acrylic acid polymer is in the range from about 2.5:1 to about 0.08:1.

2. The composition of claim 1, wherein said cross-linked acrylic acid polymer comprises one or more of acrylates copolymer and acrylates/C10-30 alkyl acrylate cross polymer.

3. The composition of claim 1, wherein said cross-linked acrylic acid polymer is present in an amount of from about 0.8 to about 2.9 weight percent of the composition.

4. The composition of claim 1, wherein said at least one of an amphoteric and/or nonionic surfactant comprises one or more of cocamidopropyl betaine, cocamidopropyl hydroxysultaine, decyl glucoside, and sodium cocoamphoacetate.

5. The composition of claim 1, wherein said at least one of an amphoteric and/or nonionic surfactant is present in an amount of from about 1.0 to about 8.0 weight percent of the composition.

6. The composition of claim 1, wherein said anionic surfactant comprises one or more of sodium lauryl sulfate, ammonium lauryl sulfate, sodium laureth sulfate, and ammonium laureth sulfate.

7. The composition of claim 1, wherein said anionic surfactant is present in an amount of from about 1.0 to about 8.0 weight percent of the composition.

8. The composition of claim 1, wherein said cationic polymer comprises quaternary ammonium hydroxyethyl cellulose and guar derivatives.

9. The composition of claim 1, wherein said cationic polymer is present in an amount of from about 0.10 to about 0.50 weight percent of the composition.

10. The composition of claim 1, wherein said ester comprises a glyceryl ester.

11. The composition of claim 10, wherein said ester comprises one or more of glyceryl oleate and PEG-7 glyceryl cocoate.

12. The composition of claim 1, wherein said ester is present in an amount of from about 0.10 to about 1.80 weight percent of the composition.

13. The composition of claim 1, wherein said polyol comprises one or more of glycerin, sorbitol, and lactose.

14. The composition of claim 1, wherein said polyol is present in an amount of from about 1.0 to about 5.0 weight percent of the composition.

15. The composition of claim 1, wherein the weight ratio of polyethylene glycol to cross-linked acrylic acid polymer in the range from about 12.5:1 to about 0.70:1.

16. A highly transparent personal cleansing composition comprising:
    a) a cross-linked acrylic acid polymer;
    b) at least one of an amphoteric or nonionic surfactant;
    c) an anionic surfactant;
    d) a cationic quaternary ammonium compound polymer;
    e) an ester;
    f) a polyol different from component (g); and
    g) a polyethylene glycol comprising from about 6 to about 12 moles of ethylene oxide, wherein component (g) is different from the nonionic surfactant of component (b), if present,
    wherein the weight ratio of anionic surfactant to cross-linked acrylic acid polymer is in the range from about 2.5:1 to about 0.08:1.

17. The composition of claim 1, further comprising one or more of: a coloring agent; a water softening agent; a UV absorber, a pH modifier, a preservative, an odor absorber, a viscosity modifier, a neutralizer, a cationic conditioning polymer, an antibacterial agent, a vitamin, a botanical extract, a skin conditioner, a moisturizer and/or mixtures thereof.

18. The composition of claim 16, wherein said cross-linked acrylic acid polymer comprises one or more of acrylates copolymer and acrylates/C10-30 alkyl acrylate cross polymer.

19. The composition of claim 16, wherein said cross-linked acrylic acid polymer is present in an amount of from about 0.8 to about 2.9 weight percent of the composition.

20. The composition of claim 16, wherein said at least one of an amphoteric and/or nonionic surfactant comprises one or more of cocamidopropyl betaine, cocamidopropyl hydroxysultaine, decyl glucoside, and sodium cocoamphoacetate.

21. The composition of claim 16, wherein said at least one of an amphoteric and/or nonionic surfactant is present in an amount of from about 1.0 to about 8.0 weight percent of the composition.

22. The composition of claim 16, wherein said anionic surfactant comprises one or more of sodium lauryl sulfate, ammonium lauryl sulfate, sodium laureth sulfate, and ammonium laureth sulfate.

23. The composition of claim 16, wherein said anionic surfactant is present in an amount of from about 1.0 to about 8.0 weight percent of the composition.

24. The composition of claim 16, wherein said cationic polymer comprises quaternary ammonium hydroxyethyl cellulose and guar derivatives.

25. The composition of claim 16, wherein said cationic polymer is present in an amount of from about 0.10 to about 0.50 weight percent of the composition.

26. The composition of claim 16, wherein said ester comprises a glyceryl ester.

27. The composition of claim 26, wherein said ester comprises one or more of glyceryl oleate and PEG-7 glyceryl cocoate.

28. The composition of claim 16, wherein said ester is present in an amount of from about 0.10 to about 1.80 weight percent of the composition.

29. The composition of claim 16, wherein said polyol comprises one or more of glycerin, sorbitol, and lactose.

30. The composition of claim 16, wherein said polyol is present in an amount of from about 1.0 to about 5.0 weight percent of the composition.

31. The composition of claim 16, wherein the weight ratio of polyethylene glycol to cross-linked acrylic acid polymer in the range from about 12.5:1 to about 0.70:1.

32. The composition of claim 16, further comprising one or more of: a coloring agent; a water softening agent; a UV absorber, a pH modifier, a preservative, an odor absorber, a viscosity modifier, a neutralizer, a cationic conditioning polymer, an antibacterial agent, a vitamin, a botanical extract, a skin conditioner, a moisturizer and/or mixtures thereof.

* * * * *